United States Patent [19]

Landman et al.

[11] Patent Number: 4,793,351
[45] Date of Patent: Dec. 27, 1988

[54] MULTI-LUMEN BALLOON CATHETER

[75] Inventors: Mark S. Landman, Sharon; Steven R. LeMott, Stoughton, both of Mass.

[73] Assignee: Mansfield Scientific, Inc., Mansfield, Mass.

[21] Appl. No.: 62,786

[22] Filed: Jun. 15, 1987

[51] Int. Cl.4 .......................................... A61M 25/00
[52] U.S. Cl. ..................................... 128/344; 604/99
[58] Field of Search .................. 128/344, 348.1, 772; 604/96–103

[56] References Cited

U.S. PATENT DOCUMENTS

| | | | |
|---|---|---|---|
| 550,238 | 11/1895 | Allen, Jr. | 604/101 X |
| 705,346 | 7/1902 | Hamilton | 128/344 |
| 1,014,228 | 1/1912 | Kellogg | 604/97 |
| 1,633,074 | 6/1927 | De Mott | 604/32 |
| 1,690,995 | 11/1928 | Pratt | 128/344 |
| 3,211,150 | 10/1965 | Foderick | 604/97 |
| 3,436,744 | 2/1969 | Ball | 128/344 |
| 3,548,805 | 12/1970 | Datsenko | 128/207.15 X |
| 3,720,199 | 3/1973 | Rishton et al. | 128/1 D |
| 3,731,691 | 5/1973 | Chen | 128/207.15 |
| 3,795,246 | 3/1974 | Sturgeon | 128/325 |
| 3,799,171 | 3/1974 | Patel | 604/99 |
| 3,931,822 | 1/1976 | Marici | 128/207.15 |
| 4,202,346 | 5/1980 | Granier | 128/658 |
| 4,292,974 | 10/1981 | Fogarty et al. | 128/344 |
| 4,335,719 | 6/1982 | Johnston | 604/97 |
| 4,597,755 | 7/1986 | Samson et al. | 604/96 |
| 4,619,274 | 10/1986 | Morrison | 128/772 |
| 4,641,654 | 2/1987 | Samson et al. | 128/344 |
| 4,684,363 | 8/1987 | Ari et al. | 128/344 |

OTHER PUBLICATIONS

American Edwards Literature.
The Advanced Cardiovascular System Literature.

Primary Examiner—Dalton L. Truluck

[57] ABSTRACT

A medical device consists of an elongated catheter having a distal portion and a proximal portion, an inflatable balloon associated with the distal portion of the catheter and a valve member associated proximally with at least one lumen communicating with the volume of the balloon. In one embodiment, the valve member has a first position for connection of the first lumen to a source of liquid for introduction into the balloon and for connection of the second lumen to atmosphere for venting of gas displaced from the balloon by the liquid, and the valve member has a second position for connection of the first and second lumens to inflation/deflation means for flow of liquid into and rapidly out of the balloon via both lumens simultaneously. In another embodiment, a valve member is associated proximally with the second lumen, the valve member having a first position for connection of the second lumen to atmosphere for venting of gas displaced from the balloon by the liquid, and the valve member having a second position for closure of the second lumen. In both embodiments, the valve member is adapted for selective adjustment as required during use of the device between the first position for venting of gas from the device and the second position. Other embodiments include a stiffening member for varying catheter stiffness, and a catheter having proximal and distal portions formed of different materials. Methods of re-venting the balloon catheter, and varying catheter stiffness during use are also described.

18 Claims, 6 Drawing Sheets

MULTI-LUMEN BALLOON CATHETER

The invention relates to medical devices having an elongated catheter and a distal balloon. The balloon is inflatable and deflatable within the body upon command by passage of inflation media through one or more lumens defined within the catheter and terminating within the volume of the balloon.

Particularly for use in the blood carrying arteries and veins of the body, the inflation media must be selected to avoid catastrophic injury to the patient should the media be accidentally released into the body, e.g., upon rupture of the balloon. Air and other gases not quickly absorbed by the blood are particularly dangerous; liquid inflation media, e.g., radiopaque contrast media, 100%, or in solution with water or saline, is typically employed. To prepare a balloon catheter for such use in the body, the balloon and catheter lumen must be filled with inflation liquid, and air purged from the system while the device is outside the body.

One prior art device, sold by Advanced Cardiovascular Systems of Temecula, Calif., employs a metal hypodermic tube, extending within the inflation/deflation lumen into the balloon, for venting air as inflation liquid is introduced; the tube is at least partially withdrawn prior to use of the device. Another device, sold by American Edwards, Santa Ana, Calif., and described in Ari et al. U.S. Pat. No. 4,684,363, has one lumen connected proximally to a detachable vent tube for purging of air as inflation fluid is introduced via a second lumen; when purging outside the body ends, the vent tube is detached and both lumens are used for inflation/deflation of the balloon.

SUMMARY OF THE INVENTION

According to one aspect of the invention, a medical device comprises an elongated catheter having a distal portion and a proximal portion, an inflatable balloon associated with the distal portion of the catheter, the catheter defining at least a first lumen and a second lumen communicating with the volume of the balloon, and a valve member associated proximally with the first and second lumens, the valve member having a first position for connection of the first lumen to a source of liquid to be introduced into the balloon and for connection of the second lumen to atmosphere for venting gas displaced from the balloon by the liquid, and the valve member having a second position for connection of both the first and second lumens to inflation/deflation means to enable flow of liquid into and rapidly out of the balloon via both the lumens simultaneously, the valve member adapted for selective adjustment between the first position for venting of gas from the device and the second position for inflation/deflation of the balloon via the first and second lumens both prior to use of the device in an inflation/deflation medical procedure and during the procedure when gas is observed in the device.

In preferred embodiments of this aspect, the invention has one or several of the following features. The catheter further defines a third lumen terminating at a port distal of the balloon. The valve member comprises a manifold having a body, first and second conduit-defining members, each conduit-defining member having distal means for connection to proximal ends of the first add second lumens, and the first conduit defining member having a proximal end adapted for connection to the means for inflation/deflation of the balloon, and a third conduit defining member interconnecting the conduits defined by the first and second conduit-defining members, the valve member, in the first position, adapted to connect, through the manifold, the means for inflation/deflation to the first lumen for delivery of liquid into the balloon, air within the balloon being displaced via the second lumen, and the valve member adapted in the second position to connect, simultaneously, through the manifold, the means for inflation/deflation to the first lumen and the second lumen, for inflation/deflation of the balloon by flow of liquid simultaneously in both the lumens, preferably the valve member comprises a valve element mounted for rotation to the first and second positions. More preferably the third conduit is defined by the manifold body, and the valve member is adapted, in a third position, to connect, through the manifold, the means for inflation/deflation to the third conduit, for displacement of air therefrom. The valve member comprises a valve element mounted to slide between the first and second positions. The third conduit is a chamber defined in the slidable valve member of predetermined small volume selected to minimize entrapment of air within the chamber. The first and second lumens defined by the catheter and extending therewithin are separated by a generally radially disposed rib element, the rib element, during deflation of the balloon, adapted to resist collapse of wall elements defining the lumens.

According to another aspect of the invention a medical device comprises an elongated catheter having a distal portion and a proximal portion, an inflatable balloon associated with the distal portion of the catheter, the catheter defining at least a first lumen and a second lumen communicating with the volume of the balloon, the first lumen adapted for connection to a source of liquid to be introduced into the balloon, and a valve member associated proximally with the second lumen, the valve member having a first position for connection of the second lumen to atmosphere for venting of gas displaced from the balloon by the liquid, and the valve member having a second position for closure of the second lumen, the valve member adapted for selective adjustment between the first position for venting of gas from the device and the second position for closure of the second lumen prior to use in an inflation/deflation medical procedure and during the procedure when gas is observed in the device.

Preferred embodiments of both of the above aspects of the invention include additional features. For example, the medical device further comprises stiffening member having a distal tip element and an elongated body, the stiffening member sized and constructed for insertion into a lumen of the catheter for axial movement therewithin for disposition of the distal tip element at a range of positions along the length of the catheter, whereby the portion of the catheter distal of the distal tip element is relatively more flexible than the portion of the catheter containing the stiffening member, and, for adjustment of the stiffness of the catheter the distal tip element is adapted for movement axially within the lumen, preferably the stiffening member is disposed in the second lumen, opposed surfaces of the lumen and the stiffening member defining an annulus for venting of gas via the second lumen. The valve member further comprises seal means disposed about the stiffening member for retarding escape of liquid during inflation/deflation of the balloon. Also, the distal tip element has a rounded distal surface, and preferably a distal segment of the stiffening member, proximal of the tip element, narrows toward the tip element. The catheter further defines a third conduit terminating at a port defined by the catheter distal of the balloon. The proximal portion of the catheter defines proximal portions of the first, second and third lumens and is formed of a first material, and the distal portion of the catheter defines a distal portion of at least the third lumen and is formed of a second different material. The distal portion of the catheter is joined to the proximal portion of the catheter in a region of the proximal end of the balloon, the first lumen terminating at a port defined by the proximal catheter portion. The distal and proximal portions of the catheter are joined in a lap weld.

According to still another aspect of the invention a medical device comprises an elongated catheter adapted to negotiate a tortuous path of varying configuration along its length, the catheter having a distal portion and a proximal portion, the catheter defining at least one lumen extending distally within the catheter from a proximal port defined by the catheter, and a stiffening member having a distal tip element and an elongated body, the stiffening member sized and constructed for insertion into the lumen for axial movement therewithin for disposition of the distal tip element at a range of positions along the length of the catheter, whereby the portion of the catheter distal of the distal tip element is relatively more flexible than the portion of the catheter containing the stiffenig member, and, for adjustment of the stiffness of the catheter, the distal tip element is adapted for movement axially within the lumen.

In preferred embodiments of this aspect of the invention, the stiffening member is disposed in the second lumen, opposed surfaces of the lumen and the stiffening member defining an annulus for venting of gas via the second lumen gas vented from the balloon. Also, the distal tip element has a rounded distal surface, and a distal segment of the stiffening member, proximal of the tip element, narrows toward the tip element.

The medical device may have the form of a percutaneous transluminal coronary angioplasty (PTCA) catheter, or of a catheter for valvuloplasty.

According to still another aspect of the invention a method for purging air from a balloon catheter comprising an elongated catheter having a distal portion and a proximal portion, an inflatable balloon associated with the distal portion of the catheter, the catheter defining at least a first lumen and a second lumen extending within the catheter and communicating with the volume of the balloon comprises orienting the balloon catheter vertically with the balloon downward, connecting a source of liquid with the proximal end of the first lumen, introducing liquid into the first lumen to flow downward in the catheter into the balloon to force air from the balloon to flow vertically upward into the second lumen, providing a valve means for the second lumen, closing the valve means when it is observed that air is purged from the balloon catheter, connecting the proximal end of the first lumen to inflation/deflation means, operating the inflation/deflation means to cause flow of liquid into and out of the balloon via the first lumen for inflating and deflating the balloon within a patient s body, and, after a series of inflation/deflation cycles, opening the valve means as required to vent further air from the balloon catheter.

In preferred embodiments of this aspect of the invention the valve means in a first position connects the first lumen to the source of inflation liquid and vents the second lumen to the atmosphere and in a second position connects the first and second lumens to the inflation/deflation means with the second lumen closed, the method further comprising placing the valve means in a first position for filling the balloon catheter with inflation liquid and venting air, thereafter placing the valve means in the second position to interconnect the first and second lumens and operating the inflation/deflation means for simultaneous flow of liquid in both the lumens, upon observation of further air in the balloon catheter, placing the valve means in the first position for further venting of air, and placing the valve means in the second position for continuation of balloon inflation/deflation treatment.

According to still another aspect of the invention a method for advancing a catheter through a passage of the body comprises providing a catheter defining a lumen extending therewithin and a stiffening member having a distal tip element and an elongated body sized and constructed for insertion into the lumen and for axial movement therewithin, inserting the catheter into a passage of the body and advancing the catheter therealong, moving the stiffening member axially relative to the catheter to adjust the axial position of the distal tip element of the stiffening member within the lumen to adjust the stiffness of the catheter, movement of the distal tip element to a position relatively more distal causing the catheter to be relating more stiff, and movement of the distal tip element to a position relatively more proximal causing the catheter to be relatively less stiff.

Objectives of the invention include providing a balloon catheter that can be easily purged of air during filling of the device with inflation liquid outside the body, and that can be simply, quickly and safely revented of residual gas discovered in the system during a medical procedure, e.g., during percutaneous transluminal coronary angioplasty (PTCA), valvuloplasty or other procedure. Another objective is to provide such a device with a valving member and at least a pair of lumens, the device with the valving member in a first position allowing one lumen to be used for filling the balloon with inflation fluid while air is vented through the second lumen, and with the valving member in a second position, allowing both lumens to be used for simultaneous flow of inflation fluid for inflation and rapid deflation of the balloon. Other objectives include providing a catheter device having variable stiffness; providing a catheter device having segments of different flexibility or other characteristics along its length; and providing a method for employing these features.

These and other features and objectives of the invention will be understood from the following description of a preferred embodiment, and from the claims.

PREFERRED EMBODIMENT

We first briefly describe the drawings.

Drawings

FIG. 8 is a plan view of still another preferred embodiment of the balloon catheter of the invention, while FIG. 8a is a similar view of a stiffener for varying the stiffness of the catheter, e.g., of FIG. 8.

Referring now to FIGS. 1 through 5, a catheter 10, e.g., sized and constructed for use in percutaneous transluminal coronary angioplasty (PTCA), as described more fully below, has an elongated body 12, connected proximally to extension tubes 19, 21, and 23 at trifurcation 24. Connected proximally to each extension tube are luer hubs 18, 20 and 22. Disposed adjacent to the distal end of body 12 is balloon 14, and, about the catheter body therewithin, two radiopaque markers 16.

Figure 1:
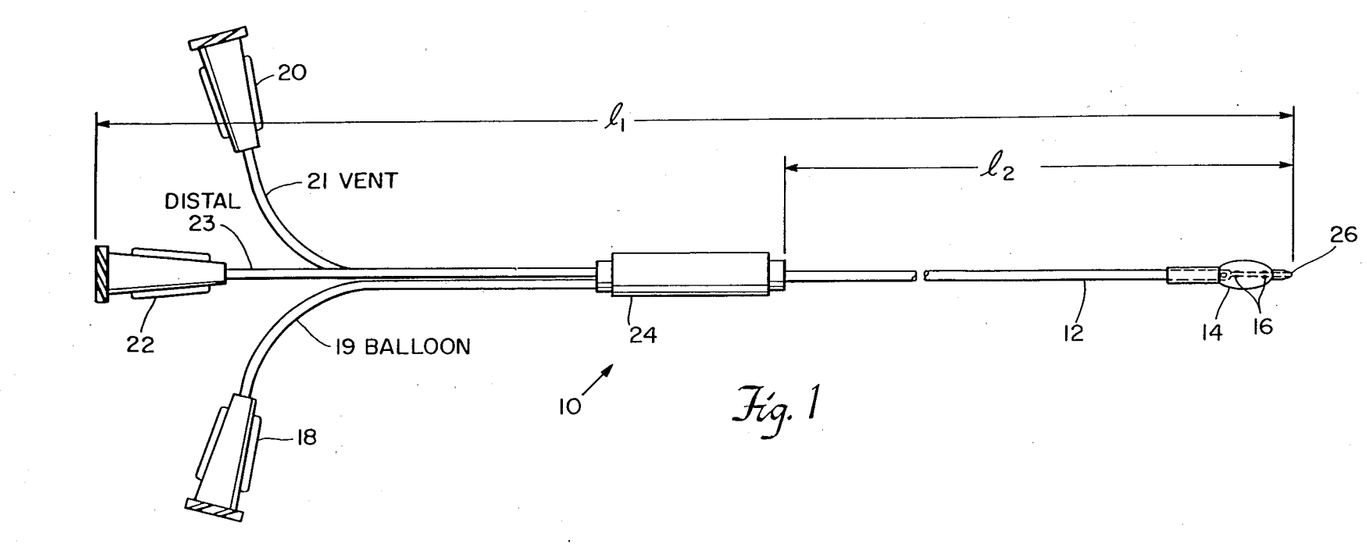
FIG. 1 is a plan view of a multi-lumen balloon catheter according to the invention.

The catheter body is of length $L_2$, e.g., 135 centimeters, to enable the device to be inserted via a puncture opening into the body at the femoral artery, to reach distal coronary artery lesions. The overall catheter length, $L_1$, including the length of the body plus the extension tubes, is, e.g., approximately 150 centimeters.

Figure 2:
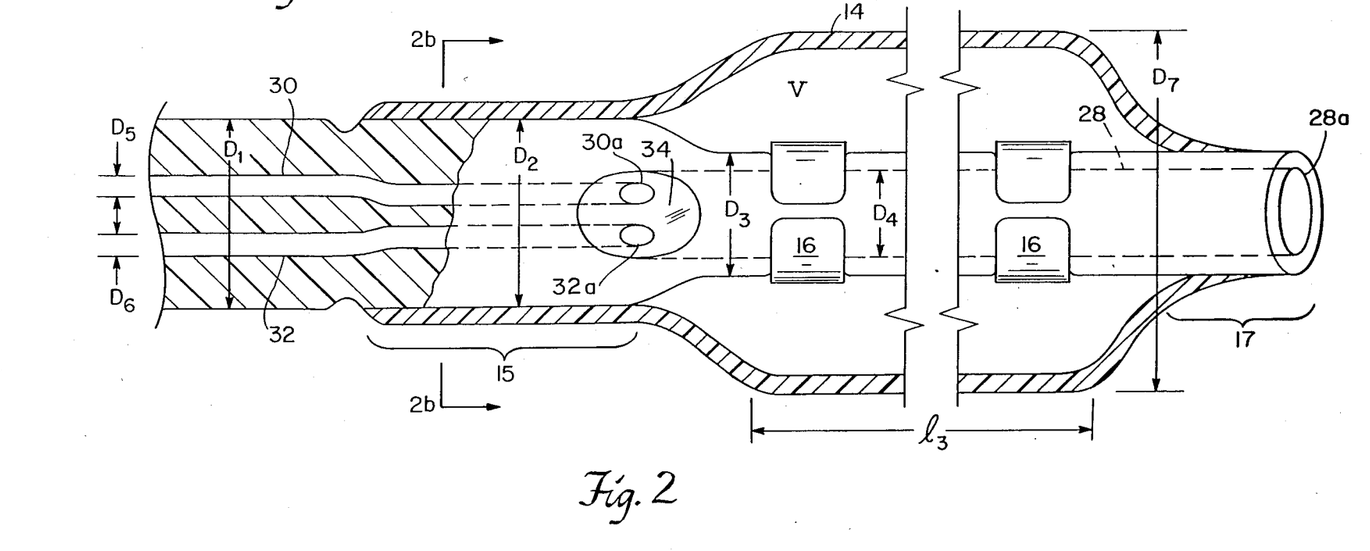
FIG. 2 is a plan view partially in section, taken on an enlarged scale, of the distal portion of the catheter of FIG. 1.
Figure 2A:
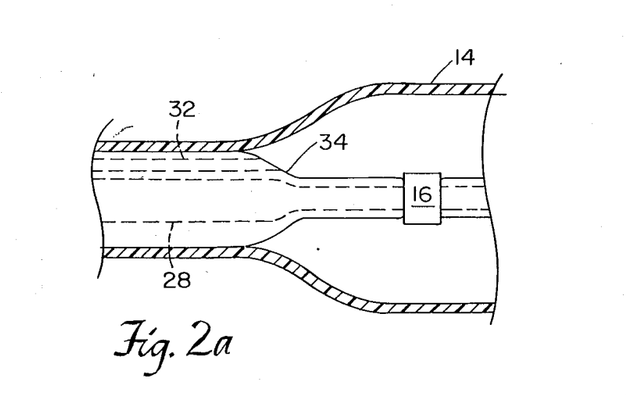
FIG. 2a is a partial side view, similar to FIG. 2, of the balloon catheter.

Balloon luer hub connector 18 at the proximal end of balloon extension tube 19 is connected to balloon lumen 30 via trifurcation 44, and terminates at balloon lumen port 30a on surface 34 at the proximal end of balloon. Leur connector 20 at the proximal end of vent extension tube 21 is connected to vent lumen 32 via trifurcation 24, and terminates at port 32a on surface 34. Ports 30a and 32a communicate to the inner volume, V, of the balloon 14. Distal luer hub 22 at the proximal end of distal extension tube 23 is connected to distal lumen 28 via trifurcation 24, and terminates at port 28a at distal tip of the catheter. Lumen 28 extends within the catheter body generally along the axis of the balloon, and does not communicate fluidically with the internal volume of the balloon. Radiopaque markers 16 within the balloon 14 provide the user with means for monitoring the location of balloon fluoroscopically during use.

Figure 2B:
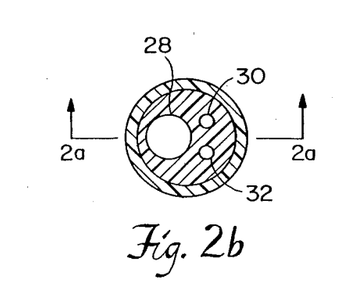
FIG. 2b is a cross sectional view taken on line 2b—2b of FIG. 2.

The outside diameter of the catheter body 12 is modified to maintain a continuous outer diameter with the balloon attached. The main (proximal) portion of the body 12 has diameter, $D_1$, approximately 0.057 inch. The diameter is reduced to $D_2$, approximately 0.044 inch, in the proximal region 15 of balloon attachment. The catheter body is further reduced i diameter distal of the termination of balloon and surface 34 defining the outlets 30a, 32a of lumens 30, 32, to diameter, $D_3$, approximately 0.032 inch. The catheter diameter remains constant distally to the region where it blends with distal region 17 of balloon attachment. The internal diameter, $D_4$, of distal lumen 28 decreases from approximately 0.029 inch immediately distal of trifurcation 24 to approximately 0.022 inch at port 28a. The internal diameters of lumens 30, 32, $D_5$ and $D_6$ respectively, decrease from approximately 0.014 inch immediately distal of trifurcation 24 to approximately 0.010 inch at surface 34 defining ports 30a and 32a.

Balloon 14 is fabricated of relatively nondistendible material, e.g., polyethylene. The balloon unfolds during use to its predetermined stated diameter, $D_7$, e.g., 2 mm to 4 mm, or perhaps greater, the corresponding deflated balloon profile varying from about 0.045 inch to 0.059 inch. The balloon length, $L_3$, in this preferred embodiment, is 2.5 centimeters.

Figure 3:
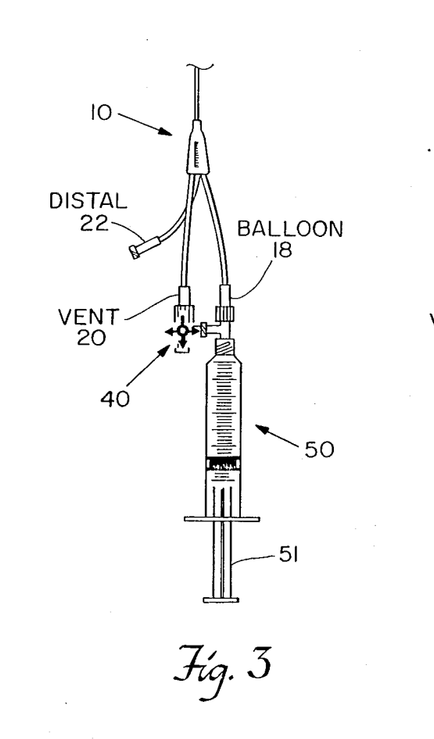
FIGS. 3, 4, and 5 are diagrammatic views illustrating the balloon catheter of FIG. 1 at different stages in use.
Figure 3A:
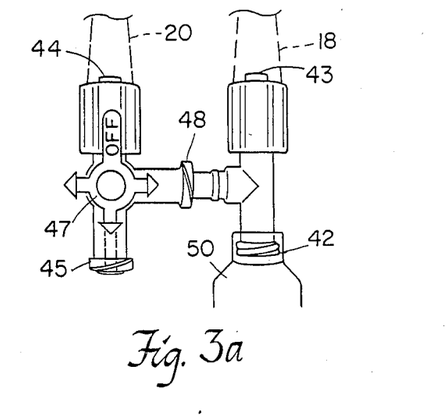
FIGS. 3a, 3b, FIGS. 4a, 4b, and FIGS. 5a, 5b illustrate the condition of the manifold at the respective stages of operation illustrated in Figs. 3, 4 and 5.
Figure 3B:
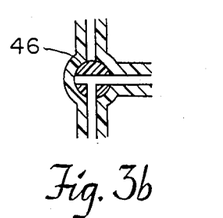
Figure 4:
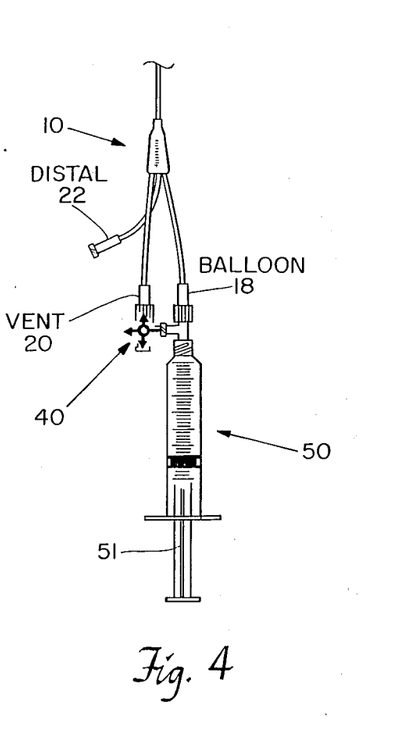
Figure 4A:
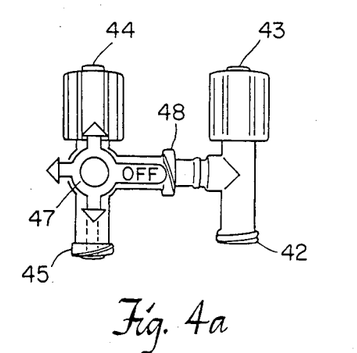
Figure 4B:
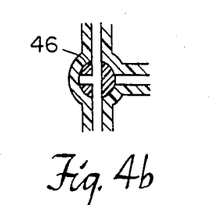
Figure 5:
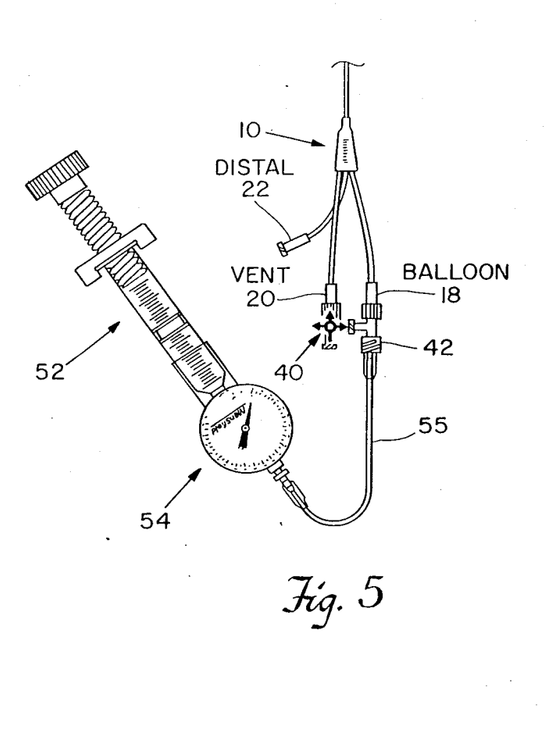
Figure 5A:
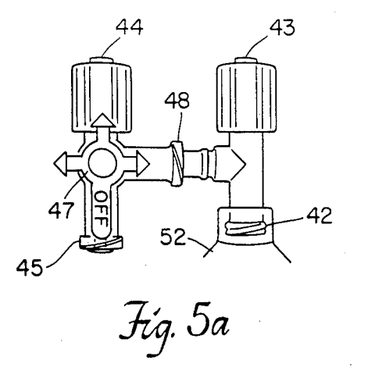
Figure 5B:
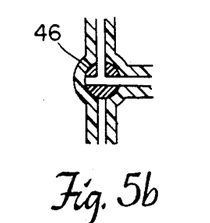

Referring now to FIGS. 3, 4 and 5 the balloon catheter is prepared by attaching accelerator or manifold 40 to luer hub connectors 18 and 20, thereby enabling connection of balloon and vent lumens 30, 32, as described below. Manifold 40 also has a port 42 for connection of an inflation/deflation means, e.g., a syringe 50. Port 43 of manifold 40 connects to vent luer hub 20. Manifold port 45 is a vent to the atmosphere, and is constructed to prevent inadvertent attachment of syringe 50. Valve rotator 47 of manifold 40 is rotatable to three different positions, shown in FIGS. 3a, 4a and 5a, to correspondingly position the valve member 46 as shown in the respective FIGS. 3b, 4b and 5b.

Manifold 40 provides ease of purging the air from catheter 10, and also connects balloon and vent lumens 30, 32 to provide for rapid inflation/deflation of balloon 14 during use. Referring again to the figures, this is accomplished by positioning valve rotator 47 as shown in FIG. 3a, such that port 44 is closed. Syringe 50, shown in FIG. 3, is filled to about 75 percent of its volume with fluid, e.g., radiopaque contrast media solution, to be used during the procedure. The syringe plunger is advanced to inject fluid through port 42, and purge air through bridge 48 and out atmospheric vent 45. After this is accomplished, valve rotator 47 is rotated to the position shown in FIG. 4a. Port 44 is now open, and bridge 48 closed. The catheter 10 is held with distal tip 26 pointed vertically downward, and the syringe plunger 51 is advanced to force fluid through balloon port 30a into the internal volume, V, of balloon 14. (The catheter tip 26 is pointed vertically downward to allow the fluid to enter the balloon from balloon port 30a, and drop by gravity to the distal end of balloon forcing air up through vent port 32a and vent lumen 32, and out through vent port 45 of manifold 40.) The purging process is continued until balloon fills, and air is purged through vent lumen 32, vent extension tube 21 and luer hub 20, and finally from vent port 45 of accelerator 40. When it is observed visually that all the air has been purged and the catheter and manifold system contain only the liquid inflation media, valve rotator 47 is rotated to the position shown in FIGS. 5a and 5b, closing vent port 45 and opening bridge 48. In this position, lumens 30, 32 are fluidically connected through port 42 to syringe 50, or via extension tube 55, to an inflation device 52 with pressure gauge 54. In the condition shown in FIGS. 5, 5a and 5b, inflation/deflation is advantageously accomplished via both lumens 30, 32.

The balloon catheter 10 of the invention, filled with inflation fluid and purged of air, is now in condition for placement within the body. For example, for PTCA, a puncture opening is provided through the skin of the leg into the femoral artery and gradually widened to a diameter necessary for introduction of the catheter, by means of the Seldinger technique. The surgeon inserts a guidewire through the opening and guides the tip fluoroscopically to a desired position adjacent a constriction or narrowing in a coronary artery. The catheter 10, with balloon 14 deflated to a small diameter, is introduced into the body along the guidewire extending through distal lumen 28 and advanced to the coronary constriction. Once the catheter is positioned, the guidewire may be removed. The balloon at the distal end of the catheter is positioned in the artery at the constriction and inflated by the surgeon to open up the narrowing, e.g., by redistribution of placgue that has caused the narrowing within the vessel. The inflated balloon of course occludes blood flow, and the patient's condition is monitored carefully throughout the procedure. The balloon is deflated to restore blood flow before damage occurs.

The procedure is most effective if extended inlfation times can be achieved, but it is critical that the balloon deflate rapidly upon command to avoid injury to the patient. During the procedure, the surgeon can monitor patient hemodynamic pressure at the site of the constriction via the distal lumen 28; and contrast media can be injected into the blood via lumen 28 for fluoroscopic examination of the area being treated. The procedure continues with the balloon repeated inflated and deflated upon command.

The balloon catheter of the invention is advantageously constructed so that, if it is observed after initial prepping or venting of air, that air is inadvertently left in the balloon or catheter, the purging procedure can be repeated by re-positioning valve rotator 47 as shown in FIGS. 3a, 4a and 5a to again purge the system of air, either within the body or outside after the catheter is temporarily withdrawn. (Pockets of air within the catheter can affect the procedure adversely by increasing inflation/deflation times, due to compressibility of the gas, and by misleading the surgeon due to the similarity on the fluoroscope of air pockets and arterial lesions.) The purging procedure can be continued until all air is purged from the balloon.

Other embodiments are within the following claims. For example, the catheter 10 coupled to manifold 40 may be used with a syringe 50, or with an inflation device 52 (constructed, e.g., as described in Leveen et al. U.S. Pat. No. 4,312,343). The catheter 10 may also be used without manifold 40, venting being accomplished through a stopcock (e.g., 86, FIG. 8) fixed to vent luer connector 20, with the syringe attached to balloon luer connector 18. The distal tip of the catheter is positioned vertically downward as previously discussed, and the syringe barrel advanced to force fluid into the balloon through port 30a, the fluid dropping vertically to the distal end of balloon, forcing air up through vent port 32a, and eventually out through the stopcock attached to vent luer connector 20. This arrangement permits rapid purging of air from the system, and re-venting of the system to remove residual air during use, but does not provide the rapid inflation/deflation times of the first embodiment because it utilizes only lumen 30 for inflation/deflation of balloon 14.

Figure 6:
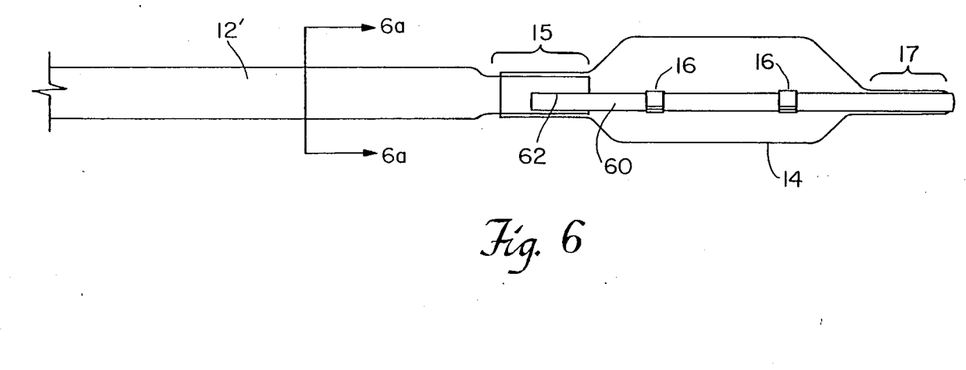
FIG. 6 is a side view of another preferred embodiment of the balloon catheter of the invention, showing the distal portion of the catheter.
Figure 6A:
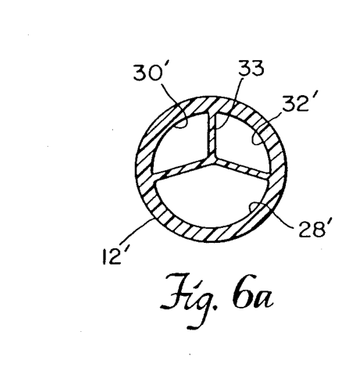
FIG. 6a is a cross sectional view taken on a line 6a—6a of FIG. 6.

In a second preferred embodiment, shown in FIGS. 6 and 6a, catheter body 12' has non-circular lumens 28', 30' and 32' to take advantage of all available space within the cross section of body 12' for lumen area. Rib 33 separating the balloon lumen 30' from vent lumen 32' provides strength to resist collapse of the walls defining these lumens during deflation of the balloon, when negative pressure is applied via syringe 50 or inflation device 52. Also, the construction of the embodiment shown in FIG. 6 has a lap weld joint at 62, under proximal balloon attachment region 15 connecting the distal portion 60 of the catheter within the balloon to the main body 12'. This permits use of different materials for portion 60 and main body 12', for example, in particular situations where it is desirable to have a proximal portion of different flexibility compared to that of the body 12'.

Figure 7:
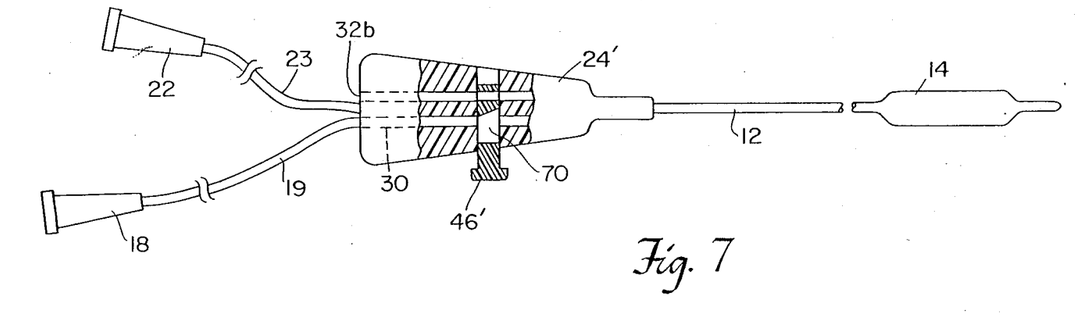
FIGS. 7 and 7a are seguential plan views, partially in section, of another preferred embodiment of the balloon catheter of the invention.
Figure 7A:
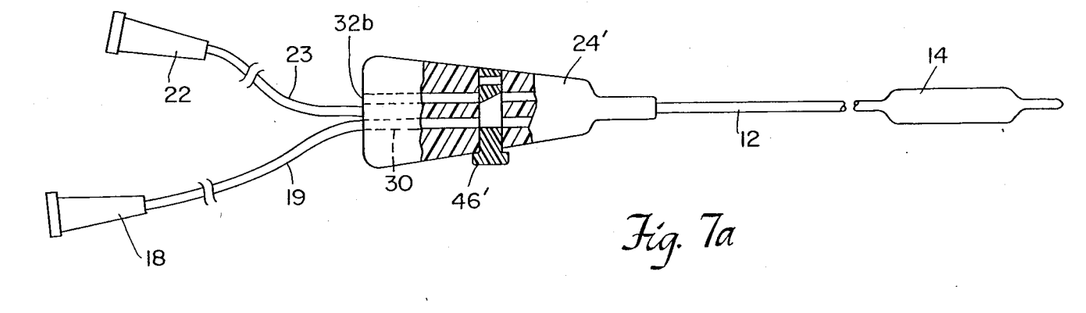

Referring now to the preferred embodiment of FIG. 7, trifurcation 24' is constructed with a sliding valve member 46' for venting, purging and preparation of the balloon catheter. In FIG. 7, venting of the balloon is achieved by positioning the valve member 46' to connect to the vent lumen 32 to vent port 32b, with the balloon lumen 30 extending separately through the trifurcation 24'. When the valve member 46' is moved to the position shown in FIG. 7a, vent port 32b is closed and balloon and vent lumens 30, 32 are interconnected via chamber 70 of valve member 46'. Chamber 70 of valve actuator 46' is designed with small volume for minimal dead volume, thereby reducing the potential of entrapment of a significant amount of air.

Figures 8, 8A:
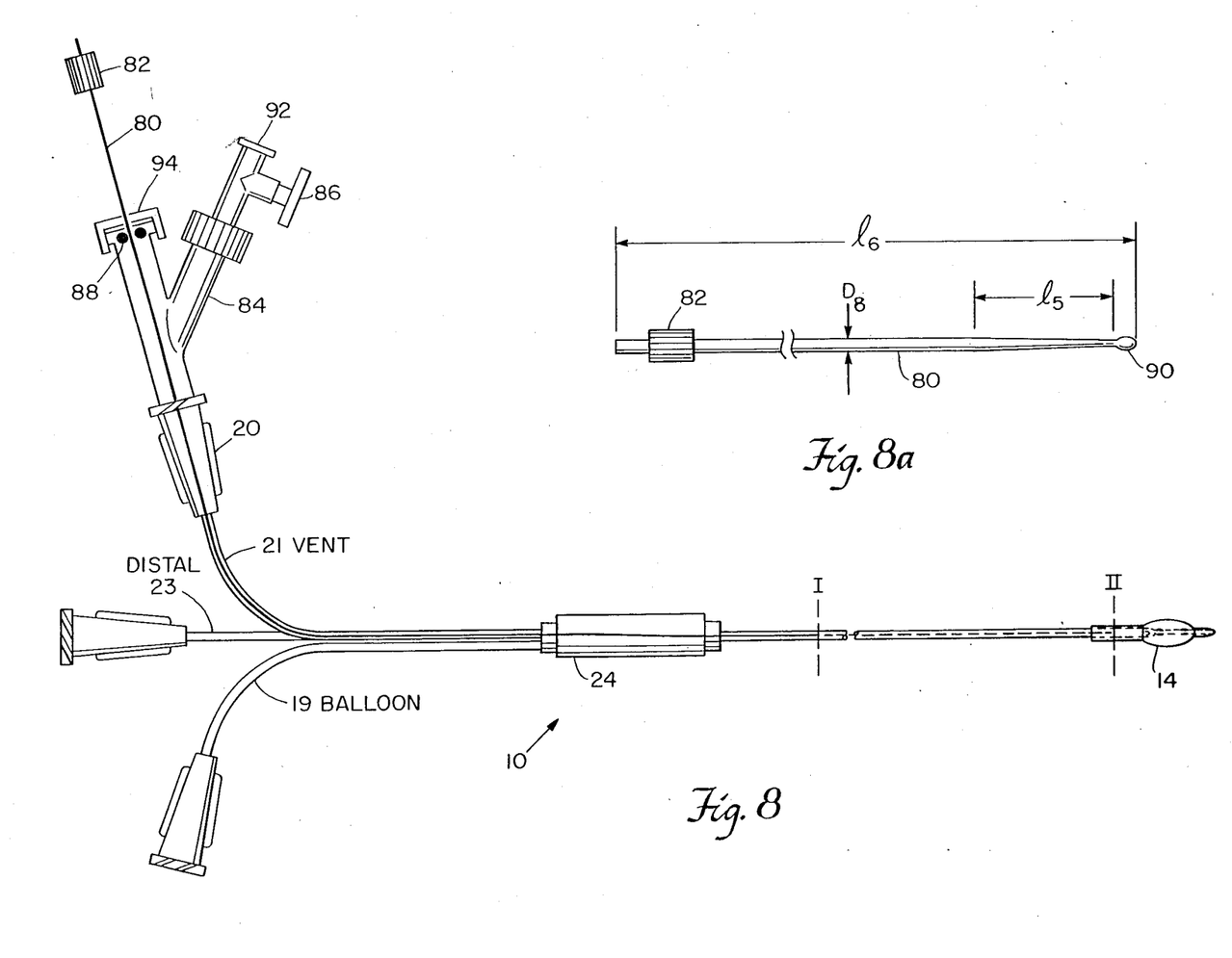

Also, referring to FIGS. 8 and 8a, another embodiment of balloon catheter 10 is shown. Wire stiffener 80 is fed through Y-connector 84 connected to vent connector 20 through trifurcation 24 into vent lumen 32. Handle 82 of stiffener 80 provides means for axial positioning of wire stiffener 80 within the lumen. O-ring 88 situated in Y-connector 84 seals fluid from leaking out around the wire 80. A one-way stopcock 86 is affixed to the second port to provide for venting of the system. FIG. 8a shows a detailed drawing of the wire stiffener 80, having an overall length, $L_6$, approximately 170 centimeters, and a tapered length, $L_5$, approximately 10 centimeters, to a rounded element 90 at the distal tip. (The tapered portion provides gradually decreasing stiffness of wire stiffener 80, the ball 90 at distal tip of the wire 80 provides a means to prevent puncture through catheter lumen 32.) Wire stiffener 80 body and ball 90 have a diameter, $D_8$, approximately 0.010 inch; the tapered portion tapers to approximately one-half of $D_8$.

During use, the stiffener 80 may be moved axially within the lumen, e.g., from position I to position II, to increase stiffness of distal portion of catheter. The stiffener can be removed or remain in the lumen during use, with the o-ring 88 providing a leak-proof seal about the wire. The catheter 10 retains purging and preparation characteristics previously discussed above, even with the wire stiffener in place, air being purged to the atmosphere along the length of stiffener through the annulus between the wall of vent lumen 32 and the surface of the wire stiffener 80, through stopcock 86 out port 92.

By way of example, the catheter of the invention is described and dimensioned for use in a PTCA procedure; the device may be sized and constructed for other medical procedures employing balloon catheters, e.g., for valvuloplasty, the balloon diameter may be 10 to 30 mm.

What is claimed is:
1. A medical device comprising
   an elongated catheter having a distal portion and a proximal portion,
   an inflatable balloon associated with the distal portion of said catheter,
      said catheter defining at least a first lumen and a second lumen communicating with the volume of said balloon, and a valve member associated proximally with said first and second lumens, said valve member having a first position for connection of said first lumen to a source of liquid to be introduced into said balloon and for connection of said second lumen to atmosphere for venting gas displaced from said balloon by said liquid, and said valve member having a second position for connection of both said first and second lumens to inflation/deflation means to enable flow of liquid into and rapidly out of said balloon via both said lumens simultaneously, said valve member defining, with said first lumen and said second lumen of said catheter, a closed system wherein said valve member remaining connected to said first lumen and to said second lumen in said first position and in said second position, and said medical device further comprising means for venting of residual gas from within said medical device during use of said device in an inflation/deflation procedure, said means for venting of residual gas comprising said valve member, said valve member adapted for selective adjustment, both prior to use of said device in the inflation/deflation medical procedure, and during the inflation/deflation procedure, for venting residual gas from within the device, between said first position for venting of gas from said device and said second position for inflation/deflation of said balloon via said first and second lumens.

2. The medical device of claim 1 wherein said catheter further defines a third lumen termininating at a port distal of said balloon.

3. The medical device of claim 1 wherein said valve member comprises a manifold having a body, first and second conduit-defining members, each said conduit-defining member having distal means for connection to proximal ends of said first and second lumens, and said first conduit-defining member having a proximal end adapted for connection to said means for inflation/deflation of said balloon, and a third conduit-defining member interconnecting the conduits defined by said first and second conduit-defining members, said valve member, in said first position, adapted to connect, through said manifold, said means for inflation/deflation to said first lumen for delivery of inflation liquid into said balloon, air within said balloon being displaced via said second lumen, and said valve member adapted in said second position to connect, simultaneously, through said manifold, said means for inflation/deflation to said first lumen and said second lumen, for inflation/deflation of said balloon by flow of inflation liquid simultaneously in both said lumens.

4. The medical device of claim 3 wherein said valve member comprises a valve element mounted for rotation to said first and second positions.

5. The medical device of claim 4 wherein the third conduit is defined by said manifold body, and said valve member is adapted, in a third position, to connect, through said manifold, said means for inflation/deflation to said third conduit, for displacement of air therefrom.

6. The medical device of claim 3 wherein said valve member comprises a valve element mounted to slide between said first and second positions.

7. The medical device of claim 5 wherein the third conduit is a chamber defined in the slidable valve member, said chamber being of predetermined small volume selected to minimize entrapment of air within said chamber.

8. The medical device of claim 1 wherein said first and second lumens defined by said catheter and extending therewithin are separated by a generally radially disposed rib element, said rib element, during deflation of said balloon, adapted to resist collapse of wall elements defining said lumens.

9. A medical device of claim 1 further comprising a stiffening member having a distal tip element and an elongated body, said stiffening member sized and constructed for insertion into a lumen of said catheter for axial movement therewithin for disposition of said distal tip element at a range of positions along the length of said catheter, whereby the portion of said catheter distal of said distal tip element is relatively more flexible than the portion of said catheter containing said stiffening member, and, for adjustment of the stiffness of said catheter, the distal tip element is adapted for movement axially within said lumen.

10. The medical device of claim 9 wherein said stiffening member is disposed in said second lumen, opposed surfaces of said lumen and said stiffening member defining an annulus for venting of gas via said second lumen.

11. The medical device of claim 9 wherein said valve member further comprises seal means disposed about said stiffening member for retarding escape of liquid during inflation/deflation of said balloon.

12. The medical device of claim 9 wherein said distal tip element has a rounded distal surface.

13. The medical device of claim 12 wherein a distal segment of said stiffening member, proximal of said tip element, narrows toward said tip element.

14. A medical device of claim 2 wherein the proximal portion of said catheter defines proximal portions of said first, second and third lumens and is formed of a first material, and the distal portion of said catheter defines a distal portion of at least said third lumen and is formed of a second different material.

15. The medical device of claim 14 wherein said distal portion of said catheter is joined to said proximal portion of said catheter in a region of the proximal end of said balloon, said first lumen terminating at a port defined by said proximal catheter portion.

16. The medical device of claim 14 wherein said distal and proximal portions of said catheter are joined in a lap weld.

17. A method for purging air from an inflatable medical device, said method comprising A. providing an inflatable balloon catheter comprising an elongated catheter having a distal portion and a proximal portion, an inflatable balloon associated with the distal portion of said catheter, said catheter defining at least a first lumen and a second lumen extending within said catheter and communicating with the volume of said balloon, and said medical device further comprising means for venting of residual gas from within said medical device during use of said device in an inflation/deflation procedure, said means for venting of residual gas comprising a valve member associated proximally with said first and second lumens and adapted for selective adjustment between a first position, for connection of said first lumen to a source of liquid to be introduced into said balloon and for connection of said second lumen to atmosphere for venting gas displaced from said balloon by said liquid, and a second position, for connection of both said first and second lumens to inflation/deflation means to enable flow of liquid into and rapidly out of said balloon via both said lumens simultaneously, said valve member defining, with said first lumen and said second lumen of said catheter, a closed system wherein said valve member remaining connected to said first lumen and to said second lumen in said first position and in said second position, B. orienting said balloon catheter vertically with said balloon downward, C. connecting a source of liquid to the proximal end of said catheter, D. adjusting said valve means to said first position for filling said balloon catheter with inflation liquid and venting air, E. introducing liquid into said catheter to flow downward in said first lumen into said balloon to force air from said balloon to flow vertically upward in said second lumen, F. connecting the proximal end of said catheter to inflation/deflation means, G. thereafter adjusting said valve means to said second position to interconnect said first and second lumens, H. operating said inflation/deflation means for flow of liquid through both said lumens simultaneously, to cause flow of liquid into and out of said balloon via said first lumen and said second lumen for inflating and deflating said balloon within a patient's body, I. after one or more inflation/deflation cycles, adjusting said valve means to said first position to vent residual air from said balloon catheter, and, thereafter, J. adjusting said valve means to said second position for continuation of balloon inflation/deflation treatment.

18. The method of claim 17 comprising the further steps of repeating Step I and Step J as required to remove residual air from the medical device during the inflation/deflation procedure.

* * * * *

UNITED STATES PATENT AND TRADEMARK OFFICE
CERTIFICATE OF CORRECTION

PATENT NO. : 4,793,351
DATED : December 27, 1988
INVENTOR(S) : Mark S. Landman, et al.

It is certified that error appears in the above-identified patent and that said Letters Patent is hereby corrected as shown below:

| | |
|---|---|
| Column 2, Line 2: | "conduit defining" should be --conduit- defining-- |
| Column 2, Line 51: | Insert -- a -- after "comprises" |
| Column 2, Line 60: | Insert -- , -- after "catheter" |
| Column 3, Lines 7-8: | Bad break on "mate-rial" |
| Column 3, Line 66: | "patient s" should be --patient's-- |
| Column 5, Line 14: | "seguential" should be --sequential-- |
| Column 5, Line 38: | "44" should be --24-- |
| Column 5, Line 59: | "reduced i diameter" should be --reduced in diameter-- |
| Column 7, Line 9 | "placgue" should be --placque-- |

Signed and Sealed this

Twenty-seventh Day of June, 1989

Attest:

DONALD J. QUIGG

Attesting Officer

Commissioner of Patents and Trademarks